United States Patent
Yoshihashi

[11] Patent Number: 5,879,287
[45] Date of Patent: Mar. 9, 1999

[54] ENDOSCOPE FOR MEDICAL USE

[75] Inventor: Tokusaburo Yoshihashi, Tokyo, Japan

[73] Assignee: Machida Endoscope Co., Ltd., Tokyo, Japan

[21] Appl. No.: 746,002

[22] Filed: Nov. 5, 1996

[30] Foreign Application Priority Data

Nov. 17, 1995 [JP] Japan .................................. 7-300341

[51] Int. Cl.⁶ .................................................. A61B 1/06
[52] U.S. Cl. ........................ 600/160; 600/121; 600/123
[58] Field of Search .................................. 600/160, 161, 600/162, 170, 172, 173, 176, 109, 110, 121, 123

[56] References Cited

U.S. PATENT DOCUMENTS

| | | | |
|---|---|---|---|
| 3,809,072 | 5/1974 | Ersek et al. .............................. | 600/121 |
| 3,855,897 | 12/1974 | Takahashi et al. ....................... | 600/160 |
| 4,878,485 | 11/1989 | Adair ........................................... | 128/6 |
| 5,325,845 | 7/1994 | Adair .................................... | 600/182 X |
| 5,347,990 | 9/1994 | Ebling et al. ........................... | 600/182 |
| 5,704,899 | 1/1998 | Milo .................................... | 600/121 X |

*Primary Examiner*—Beverly M. Flanagan
*Attorney, Agent, or Firm*—Levisohn, Lerner, Berger & Langsam

[57] ABSTRACT

The endoscope unit 1 includes a flexible tube 3 having a deflectable portion at one end and a proximal housing 4 at the other end. The deflectable portion of the flexible tube 3 has a hard tip 2 at its distal end and the tip 2 has an observation opening 11. The flexible tube 3 has a optical assembly guide channel 10, extending from the proximal housing 4 to the observation opening 11, for removably fitting an optical assembly 9. Optical assembly 9 includes a bundle of optical fibres covered by an external cover 18. The bundle of optical fibres has an objective lens 15 at one end and eyepiece 16 at the other end. A watertight sheath 19 is provided, the watertight sheath 19 being transparent near objective lens 15.

11 Claims, 4 Drawing Sheets

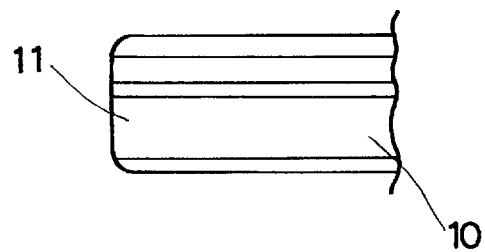
F I G. 3
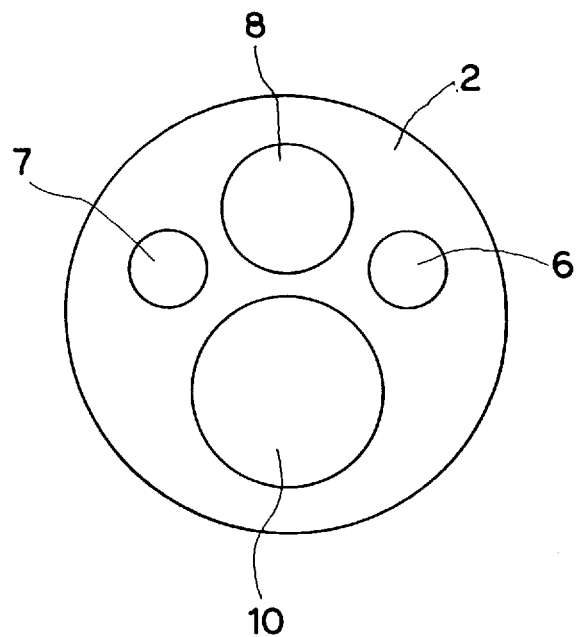
F I G. 4

ENDOSCOPE FOR MEDICAL USE

DETAILED DESCRIPTION OF THE INVENTION

1. Field of the Invention

This invention relates generally to endoscopes for medical use.

2. Description of Prior Art

An endoscope for medical use generally comprises an optical system for observation called the image, an optical system for illumination called the light guide, a flexible tube containing a forceps guide channel, a wire for controlling the tip deflection, a proximal housing containing tip deflection control and eyepiece connected to the image, and an umbilical tube containing a light guide, air/water channel, extending from the proximal housing and connected to light, air and water sources.

After using an endoscope with a construction described above, the endoscope must be cleaned and sterilized before re-use in order to prevent bacterial infections of the patients. Particularly, since the forceps guide channel is a channel open at both ends and extending over almost the entire length of the endoscope, cleaning and sterilization of the internal parts of this channel is very difficult and takes considerable time.

Since the endoscope must be cleaned and sterilized, it should have good temperature resistance, water resistance, and chemical resistance.

SUMMARY OF THE INVENTION

In this way, since cleaning and sterilizing the endoscope takes considerable time and one endoscope cannot be used continuously, endoscopes of the same number as the patients to be examined on a day must be kept ready beforehand for ensuring efficiency of examinations. This causes a tremendous financial burden and is a problem that needs to be resolved.

The method of using a sheath to cover the entire endoscope, removing the sheath after using the endoscope, replacing with a new sheath, and continuing with the use of the endoscope may be considered. However, if this method is employed, since the sheath covers the endoscope from the outside completely, the entire endoscope becomes stiff, the ease of operation of the endoscope is adversely affected, its deflectability deteriorates, and as a result, the examination takes more time imposing a larger burden on the patient and the examiner.

Another technique used is the technique of placing the forceps guide channel outside the endoscope unit to improve the cleaning and sterilization of the endoscope. However, since the forceps channel guide is outside the endoscope unit, that is, outside the control wire, the ease with which the endoscope can be operated deteriorates significantly. Moreover, the deflection state differs in different directions because of the mounting position of the forceps guide channel, which causes a major problem.

In endoscopes of the prior art, the physical resistance and the chemical resistance of the image is low. In particular, the physical resistance and the chemical resistance of the a bundle of glass fibers of the image are very low. On the contrary the image is a high-value component accounting for almost the total cost of the endoscope. Since each glass fiber forming the image is in micron units, it must be handled with extreme care when cleaning and sterilizing the endoscope, otherwise the fibers are likely to break.

Even when the endoscope has a charge-coupled device (CCD) at its tip, the physical resistance and the chemical resistance are poor.

An object of the present invention is to provide an endoscope for medical use comprising a flexible tube having a deflectable portion at one end and a proximal housing at the other end said deflectable portion of said flexible tube having a hard tip at its distal end, said tip having a forceps outlet, a light window and an observation opening, said flexible tube having a forceps guide channel extending from said proximal housing to said forceps outlet for removably fitting a forceps, a light guide channel extending from said proximal housing to said light window for fitting a light for illumination, an optical assembly guide channel extending from said proximal housing to said observation opening for removably fitting an optical assembly, said optical assembly comprising a bundle of optical fibres covered by a external cover, said bundle of optical fibres having an objective lens at one end and eyepiece at the other end, said optical assembly being covered by a watertight sheath before fitting in said optical assembly guide channel.

With the above arrangement, only the number of cleaned and sterilized endoscope units comprising the flexible tube and the proximal housing equal to the number of subjects to be examined in a day are necessary, while one or a plurality of optical assemblies, if necessary, may be used. The optical assembly is inserted in the watertight sheath, and the optical assembly and the sheath is then inserted in the optical assembly guide channel of the flexible tube and the rear end of the optical assembly is inserted and fixed in the proximal housing. When the optical assembly is inserted in the optical assembly guide channel, it blocks the observation opening in the flexible tube. Such an assembly can be used in the same manner as a conventional endoscope.

After use, the optical assembly in the sheath is pulled out of the endoscope unit, the optical assembly is pulled out of the sheath, then the optical assembly is inserted in an unused, cleaned and sterilized watertight sheath, and the optical assembly and the sheath can be inserted in an unused, cleaned and sterilized endoscope unit unabling immediate and continuous use of the endoscope. Other unused endoscope units can also be used similarly for examining patients sequentially. Used endoscope units and unused endoscope units can be differentiated and stored, and one day's lot of used endoscope units can be cleaned and sterilized in one batch.

BRIEF DESCRIPTION OF THE DRAWINGS

FIG. 3: Enlarged cross-section view of tip of the flexible tube.

FIG. 4: Front view of tip.

SPECIFIC DESCRIPTION OF THE PREFERRED EMBODIMENTS

Figure 1:
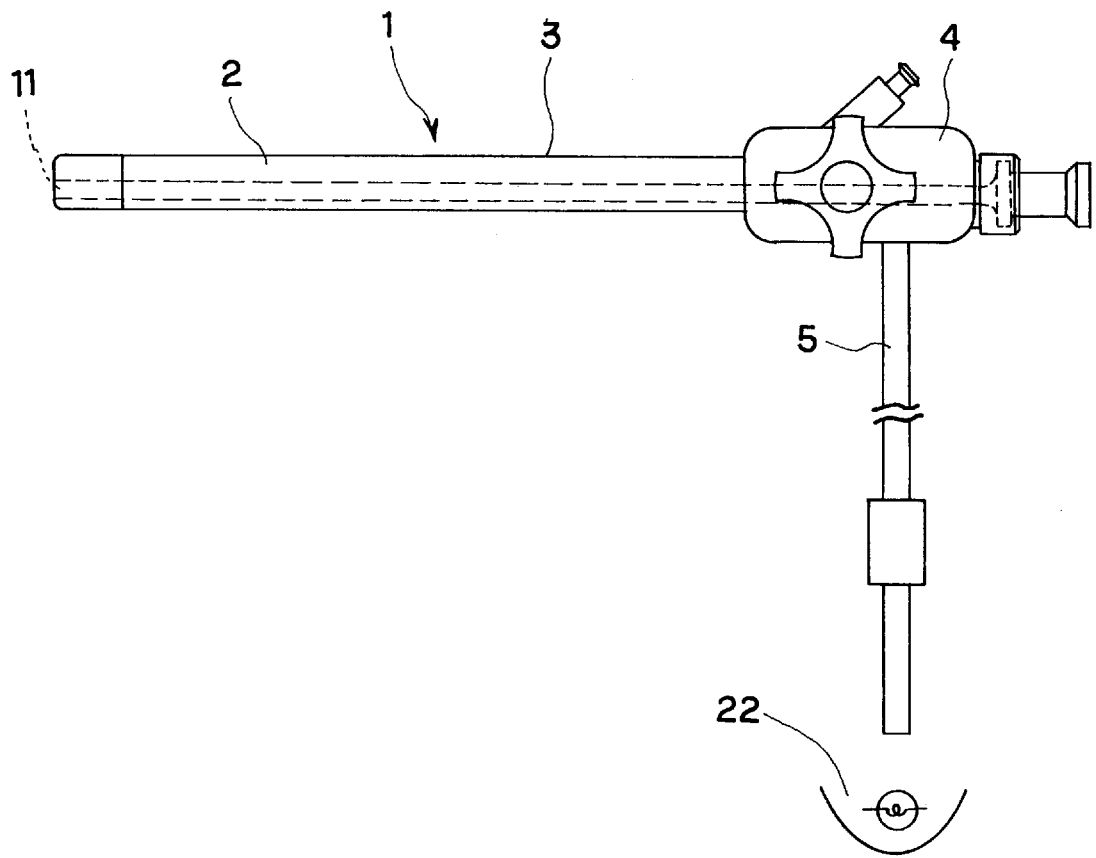
FIG. 1: Explanatory drawing of the embodiment with the optical assembly inserted.

The preferred embodiment of the invention is explained below referring to the drawings.

Figure 2:
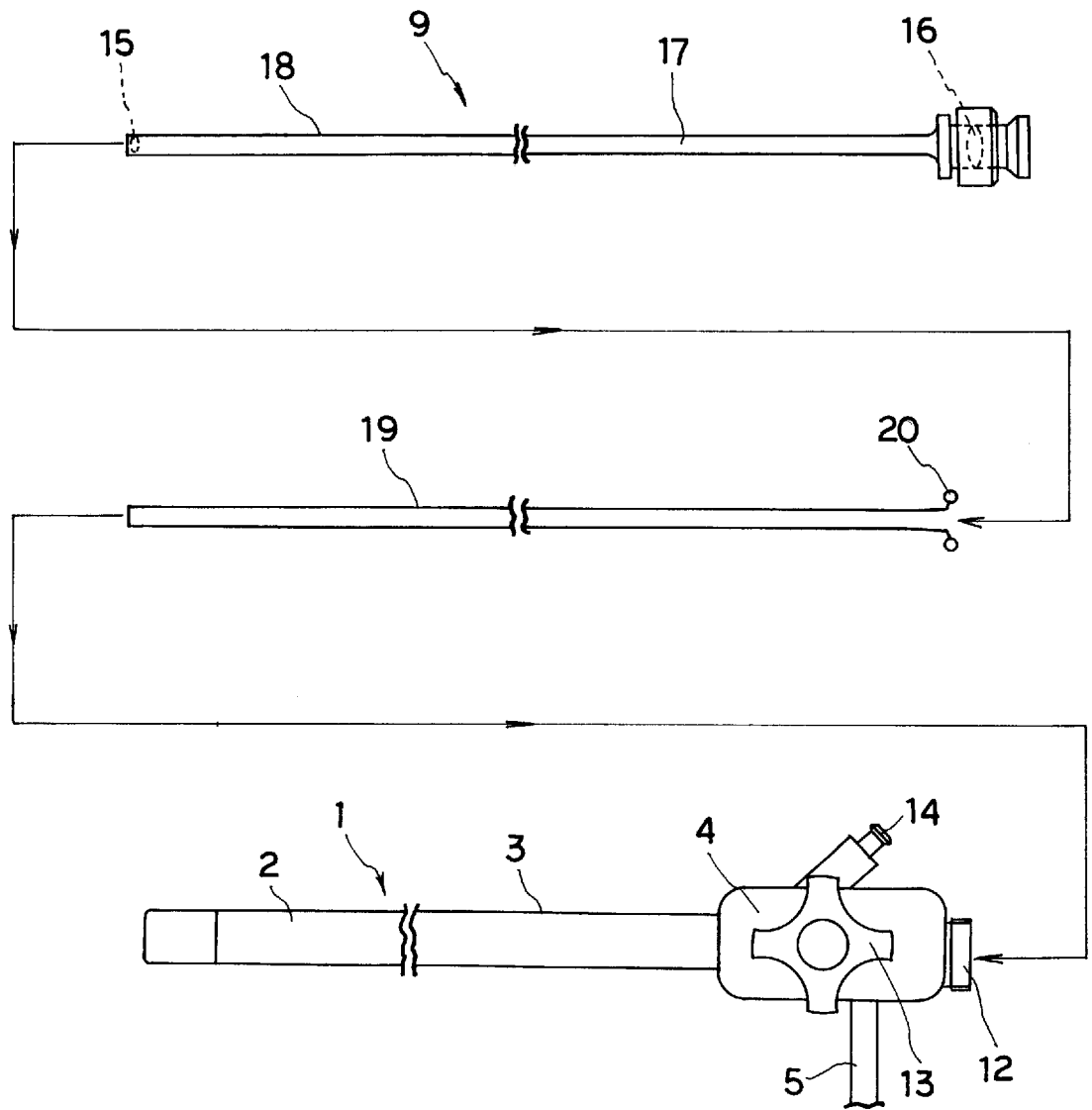
FIG. 2: Explanatory drawing of the embodiment with the optical assembly removed.

FIG. 1 is an explanatory drawing of the endoscope unit 1 with the optical assembly 9 inserted, FIG. 2 is an explanatory drawing of the endoscope unit 1 with the optical assembly 5 removed, FIG. 3 is the expanded cross section view of the tip of the flexible tube 3, and FIG. 4 is the elevation view of the hard tip 2. In these figures, 4 is a proximal housing, and 5 is an umbilical tube containing a light guide, air/water supply channels.

The hard tip 2 and the flexible tube 3 contain a light guide 6, air/water channel 7, forceps guide channel 8, and the wire for controlling the tip deflection. The optical assembly guide channel 10 into which the optical assembly 9 is inserted, extends from a observation opening 11 in the hard tip 2, passes through length of the flexible tube 3 to the proximal housing 4. The rear end of the optical assembly guide channel 10 forms an open end 12. A control knob 13 is provide to control and operate the wire. Forceps insertion inlet 14 is provided for inserting the forceps. Required light for illumination is supplied by the light source 22.

The internal diameter of the optical assembly guide channel 10 near the observation opening 11 is made little smaller that the outer diameter of the hard tip 2 of the optical assembly 9. Because of this when the optical assembly 9 is inserted in the optical assembly guide channel 10 the hard tip 2 touches the optical assembly guide channel 10 and fits stably.

As shown in FIG. 2, the optical assembly 9 has an objective lens 15 at the front end of a bundle of optical fibers 17, and an eyepiece 16 fitted at the rear end. The fiber bundle 17 is covered with an external tube 18 from the objective lens 15 to the eyepiece 16 providing a waterproof construction.

The optical assembly 9 is inserted in the optical assembly guide channel 10 of the endoscope unit 1. If the optical assembly 9 is too soft, difficulty will arise at the time of insertion. Therefore, material that has some stiffness and resilience, and whose surface can slide in easily, is recommended. If the stiffness or resilience is too high, the deflectability of the endoscope unit into which the optical assembly is inserted, may be adversely affected. A metallic or plastic wire may be built-in, using a shape memory alloy for the metallic wire, so that an electric current can be passed through to vary the temperature and thereby the hardness at the time of removal or insertion.

The rear end of optical assembly 9 can be removably fitted in the open end 12 of the proximal housing 4 of said endoscope unit 1. The open end 12 is generally located at the rear end of the proximal housing 4, but it may sometimes be located at the center of the proximal housing 4.

Figure 5:
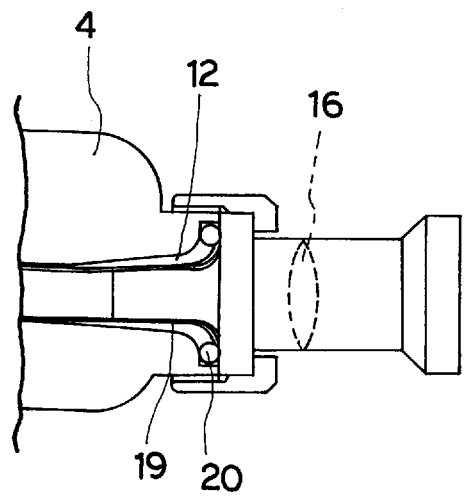
FIG. 5: Enlarged cross-section view of rear end of the optical assembly after fitting in the proximal housing.

19 is a watertight sheath for inserting the optical assembly 9 thereby protecting the optical assembly 9. The portion of the watertight sheath 19 near the objective lens 15 is made transparent so that it does not hinder the light entering the objective lens 15. The portion of the watertight sheath 19 near the objective lens 15 can be made transparent by using a glass or a transparent plastic at that portion. As shown in FIG. 5, a seal 20 that fits in between the rear end of the optical assembly 9 and the open end 12 in the proximal housing 4 is provided on the rear end of the watertight sheath 19, thereby preventing the contact of any liquids entering the optical assembly guide channel 10 through the observation opening 11 with the optical assembly 9.

In the above, an optical assembly 9 comprising a bundle of optical fiber bundle is explained. However, an optical assembly comprising a charge-coupled device (CCD) connected to an end of a electric wire may be used. In such a case, the other end of the electric wire is extended outside the endoscope unit and connected to an optical assembly processing apparatus.

Figure 6:
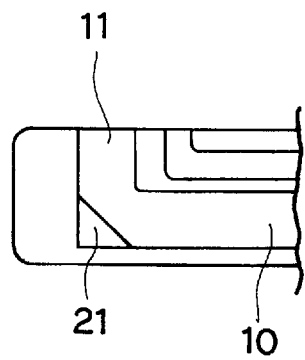
FIG. 6: Enlarged cross-section view of tip of the flexible tube in a side-vision type of endoscope.

In the above, a direct-vision type of endoscope is explained. However, the present invention can be applied to a side-vision type of endoscope shown in FIG. 6, in which the observation opening 11 is provided on the side face of the hard tip 2. In this case a reflecting element 21 like a reflecting mirror or a reflecting prism is installed near the observation opening 11 in such a way that when the optical assembly 9 is inserted in the endoscope unit 1 the eyepiece 16 faces the reflecting unit 21.

With the configuration described above, cleaned and sterilized endoscope units 1 and watertight sheaths 19 of a number equivalent to the number of patients to be examined on a day are kept ready, together with one or a plurality of optical assemblies 9.

Then the optical assembly 9 is inserted in a watertight sheaths 19, thereby covering whole of the optical assembly 9 other than the rear end. The optical assembly 9 covered by the watertight sheaths 19 is inserted in the optical assembly guide channel 10 of the endoscope unit 1, and the rear end of the optical assembly 9 is inserted and locked in the open end 12 in the proximal housing 4. When the optical assembly 9 is inserted in the optical assembly guide channel 10, it blocks the observation opening 11 in the flexible tube 3.

By assembling the elements as described above, the endoscope can be used similar to conventional endoscopes. If a plurality of optical assemblies 9 are kept ready, the examinations can proceed smoothly if the next optical assembly 9 is inserted beforehand in a watertight sheath 19 and then in the optical assembly guide channel 10 of the endoscope unit 1 to be used next.

If the endoscope malfunctions during use, the endoscope unit 1 can be replaced immediately since one unit is always kept ready, thereby protecting the patient against risks of delayed examination or delayed treatment.

After the examination is over, optical assembly 9 and the watertight sheath 19 are pulled out from the endoscope unit 1, then the optical assembly 9 is pulled out of the watertight sheath 19. Then the optical assembly 9 is inserted in an unused watertight sheath 19 and then the optical assembly 9 and the watertight sheath 19 are inserted in an unused endoscope unit 1, enabling immediate use of the endoscope similar to the above. A similar procedure can be adopted for other unused endoscope units 1 and unused watertight sheaths 19, and patients can be examined sequentially. Used endoscope units 1 should be marked and stored separately from unused ones, so that all used endoscope units 1 in a day can be collected, cleaned and sterilized in one batch. Used watertight sheath 19 are disposed.

Moreover, if a used endoscope unit 1 needs to be disposed or incinerated because of epidemiological reasons, the financial burden is minimal because optical assembly 9 which is a very expensive element is not included in the endoscope unit to be disposed.

According to the detailed explanations of the present invention above, by providing an endoscope unit comprising a flexible tube having a deflectable portion at one end and a proximal housing at the other end, said deflectable portion of said flexible tube having a hard tip at its distal end, said tip having a forceps outlet, a light window and an observation opening, said flexible tube having a forceps guide channel extending from said proximal housing to said forceps outlet for removably fitting a forceps, a light guide channel extending from said proximal housing to said light window for fitting a light for illumination, an optical assembly guide channel extending from said proximal housing to said observation opening for removably fitting an optical assembly, said optical assembly comprising a bundle of optical fibres covered by a external cover, said bundle of optical fibres having an objective lens at one end and eyepiece at the other end, said optical assembly being covered by a watertight sheath before fitting in said optical assembly guide channel, an economical endoscope unit can be offered, and by keeping ready only one optical assembly, whose cost is expensive, a number of endoscope units kept ready for use, can be used continuously for examining patients at economic costs.

The present invention also has the advantage of ease of operation in comparison to the conventional endoscopes. Moreover, since an optical assembly with low physical resistance and low chemical resistance is not integrated into the endoscope unit, cleaning and sterilization can be selected from a wide range of methods, enabling the endoscope unit to be cleaned and sterilized satisfactorily. In addition, since the endoscope unit is not used continuously, sufficient time can be allotted to its cleaning and sterilization.

Another advantageous effect is that if the endoscope malfunctions during use, it can be replaced with another immediately because a spare endoscope unit is always kept ready, thereby protecting the patients against risks of delayed examination and delayed treatment.

Furthermore, since the watertight sheath covers only the optical assembly the flexibility of the endoscope unit is not remains affected, thereby effecting a similar ease of operation as the endoscope of the prior art.

It is claimed:

1. An endoscope for medical use comprising:
   a flexible tube having a deflectable portion at one end and a proximal housing at the other end,
   said deflectable portion of said flexible tube having a hard tip at its distal end, said tip having a forceps outlet, a light window and an observation opening, said flexible tube having:
      a forceps guide channel extending from said proximal housing to said forceps outlet for removably fitting a forceps,
      a light guide channel extending from said proximal housing to said light window for fitting a light for illumination,
      an optical assembly guide channel extending from said proximal housing to said observation opening for removably fitting an optical assembly,
   said optical assembly comprising a bundle of optical fibres covered by a external cover, said bundle of optical fibres having an objective lens at one end and eyepiece at the other end; and
   a removable watertight sheath sealingly placeable around said optical assembly before fitting said optical assembly in said optical assembly guide channel.

2. An endoscope for medical use comprising:
   a flexible tube having a deflectable portion at one end and a proximal housing at the other end,
   said deflectable portion of said flexible tube having a hard tip at its distal end, said tip having a light window and an observation opening,
   said flexible tube having;
      a light guide channel extending from said proximal housing to said light window for fitting a light for illumination,
      an optical assembly guide channel extending from said proximal housing to said observation opening for removably fitting an optical assembly,
   said optical assembly comprising a bundle of optical fibres covered by a external cover, said bundle of optical fibres having an objective lens at one end and eyepiece at the other end; and
   a removable watertight sheath sealingly placeable around said optical assembly before fitting said optical assembly in said optical assembly guide channel.

3. An endoscope for medical use comprising:
   a flexible tube having a deflectable portion at one end and a proximal housing at the other end,
   said deflectable portion of said flexible tube having a hard tip at its distal end, said tip having an observation opening,
   said flexible tube having:
      an optical assembly guide channel extending from said proximal housing to said observation opening for removably fitting an optical assembly,
   said optical assembly comprising a bundle of optical fibres covered by a external cover, said bundle of optical fibres having an objective lens at one end and eyepiece at the other end; and
   a removable watertight sheath sealingly placeable around said optical assembly before fitting said optical assembly in said optical assembly guide channel.

4. An endoscope for medical use comprising:
   a flexible tube having a deflectable portion at one end and a proximal housing at the other end,
   said deflectable portion of said flexible tube having a hard tip at its distal end, said tip having a forceps outlet, a light window and an observation opening,
   said flexible tube having;
      a forceps guide channel extending from said proximal housing to said forceps outlet for removably fitting a forceps,
      a light guide channel extending from said proximal housing to said light window for fitting a light for illumination,
      an optical assembly guide channel extending from said proximal housing to said observation opening for removably fitting an optical assembly,
   said optical assembly comprising a charged-coupled device fitted at the front end of an electric wire; and
   a removable watertight sheath sealingly placeable around said optical assembly before fitting said optical assembly in said optical assembly guide channel.

5. An endoscope for medical use comprising:
   a flexible tube having a deflectable portion at one end and a proximal housing at the other end,
   said deflectable portion of said flexible tube having a hard tip at its distal end, said tip having a light window and an observation opening,
   said flexible tube having;
      a light guide channel extending from said proximal housing to said light window for fitting a light for illumination,
      an optical assembly guide channel extending from said proximal housing to said observation opening for removably fitting an optical assembly,
   said optical assembly comprising a charged-coupled device fitted at the front end of an electric wire; and
   a removable watertight sheath sealingly placeable around said optical assembly before fitting said optical assembly in said optical assembly guide channel.

6. An endoscope for medical use comprising:

a flexible tube having a deflectable portion at one end and a proximal housing at the other end, said deflectable portion of said flexible tube having a hard tip at its distal end, said tip having an observation opening, said flexible tube having:
an optical assembly guide channel extending from said proximal housing to said observation opening for removably fitting an optical assembly, said optical assembly comprising a charged-coupled device fitted at the front end of an electric wire; and a removable watertight sheath sealingly placeable around said optical assembly before fitting said optical assembly in said optical assembly guide channel.

7. An endoscope for medical use as in any of claims 1–6, wherein said optical assembly guide channel proximally terminates with a flange, said endoscope further comprising a seal disposed on a proximal end of said sheath, wherein said seal abuts said flange and seals said proximal end of said sheath.

8. An endoscope for medical use as in any of claims 1–3, wherein the portion of said sheath near the objective lens is transparent to such an extent that it does not cause hindrance to the observation.

9. An endoscope for medical use as in any of claims 4–6, wherein the portion of said sheath near the charged-coupled device is transparent to such an extent that it does not cause hindrance to the observation.

10. An endoscope for medical use as in any of claims 1–6, wherein said removable watertight sheath is disposable.

11. An endoscope for medical use comprising:

a flexible tube having a deflectable portion at one end and a proximal housing at the other end, said deflectable portion of said flexible tube having a hard tip at its distal end, said tip having a forceps outlet, a light window and an observation opening, said flexible tube having:
an optical assembly guide channel extending from said proximal housing to said observation opening for removably fitting an optical assembly, said optical assembly comprising one of
1) a charged-coupled device fitted at the front end of an electric wire, and
2) a bundle of optical fibres covered by a external cover, said bundle of optical fibres having an objective lens at one end and eyepiece at the other end; and a watertight sheath sealingly placeable around said optical assembly before fitting said optical assembly in said optical assembly guide channel, wherein said optical assembly guide channel proximally terminates with a flange, said endoscope further comprising a seal disposed on a proximal end of said sheath, wherein said seal abuts said flange and seals said proximal end of said sheath.

* * * * *